United States Patent [19]

Leacock

[11] 4,191,710

[45] Mar. 4, 1980

[54] TREATMENT OF METHACROLEIN-CONTAINING GASES

[75] Inventor: James Leacock, New York, N.Y.

[73] Assignee: Halcon Research and Development Corp., New York, N.Y.

[21] Appl. No.: 830,736

[22] Filed: Sep. 6, 1977

[51] Int. Cl.² .................. C07C 4/02; C07C 45/16
[52] U.S. Cl. .................. 260/601 R; 260/603 C; 260/604 R
[58] Field of Search ........... 260/603 C, 603 R, 601 R, 260/604 R

[56] References Cited

U.S. PATENT DOCUMENTS

| | | | |
|---|---|---|---|
| 3,162,514 | 12/1964 | Roelen | 55/31 |
| 3,218,357 | 11/1965 | Roeben | 260/601 R |
| 3,828,099 | 8/1974 | Sato | 260/601 R |
| 3,972,920 | 8/1976 | Ishii et al. | 260/531 R |

Primary Examiner—Werren B. Lone
Attorney, Agent, or Firm—William C. Long; David Dick; Riggs T. Stewart

[57] ABSTRACT

Water is removed from the methacrolein-containing effluent produced by the catalytic oxidation of isobutylene or tertiary butyl alcohol by quenching the effluent in water in a plurality of quenching steps under graduated increasing pressure.

2 Claims, 1 Drawing Figure

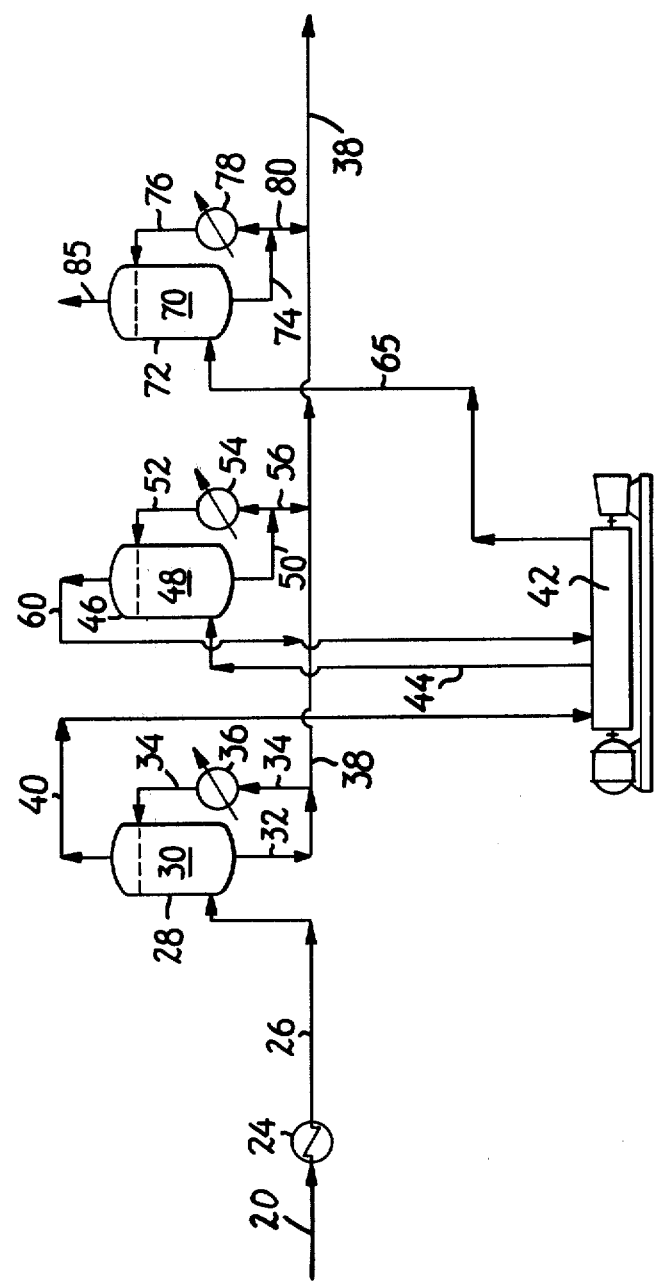

TREATMENT OF METHACROLEIN-CONTAINING GASES

This invention relates to the recovery of methacrolein from a gas mixture containing it produced by the catalytic oxidation of isobutylene or tertiary butyl alcohol.

The preparation of methacrolein by the catalytic oxidation of isobutylene, or of tertiary butyl alcohol, which is dehydrated to isobutylene in the reaction zone, is a known reaction described, for example, in Ishii et al, U.S. Pat. No. 3,972,920. In processes of this type, isobutylene or tertiary butyl alcohol are typically mixed with oxygen, e.g. as air, an inert gas such as nitrogen, carbon dioxide, and the like, and steam, and the resulting mixture is oxidized at temperatures generally ranging between 300° C. and 500° C. in the presence of a suitable catalyst, such as the one described in the above-mentioned patent, the gaseous reaction product comprising, in addition to methacrolein, unreacted isobutylene, unreacted oxygen, large amounts of inert gas and steam and minor amounts of organic by-products such as aldehydes, aliphatic acids, ketones, and the like. In some known processes for the recovery of the product methacrolein, which is in rather low concentration, e.g. less than 5 volume percent, generally 2–3 percent, the gaseous reaction mixture is treated in order to concentrate the methacrolein by condensing the water contained in the gaseous effluent. For this purpose the effluent is subjected to a series of cooling stages, for example as described in Roelen et al, U.S. Pat. No. 3,162,514. Such a process requires the use of refrigerants in order to obtain the low sub-zero temperatures which are proposed in order to obtain adequate separation of water from the reaction mixture. This method of operation has disadvantages from an economic standpoint and requires extensive refrigerating means.

It is accordingly an object of this invention to provide an improved method of separating water from the gaseous methacrolein-containing stream obtained by the catalytic oxidation of isobutylene or tertiary butyl alcohol.

It is a further object of the invention to provide an improved process of the character indicated which effectively separates water without requiring the use of refrigerants.

It is a still further object of the invention to provide a process for producing a substantially water-free gaseous methacrolein-containing stream from which the methacrolein can be readily recovered.

Other objects and features of the invention will be apparent from the following detailed description of the invention and of illustrative embodiments thereof.

In accordance with the invention, the gaseous methacrolein-containing stream which is produced by the catalytic oxidation of isobutylene or tertiary butyl alcohol is treated to separate its water vapor content and to produce a substantially anhydrous methacrolein-containing vapor stream by subjecting the gaseous stream from the catalytic reactor to a plurality of condensing or quenching stages at graduated increased pressures with the maximum pressure occurring in the final stage. The gaseous stream also suitably undergoes some cooling, but no refrigeration is necessary. Yet, the water vapor content of the gaseous stream is reduced to a very low value. Moreover, in each of the stages, i.e. in each of the plurality of condensing or quenching zones, the liquid water is recirculated to maintain a continuous body of the liquid water into which the gaseous stream to be treated is introduced so that condensation or quenching takes place by direct liquid contact rather than by surface cooling. As a result, the methacrolein content and the possibility of polymerization are minimized.

The catalytic oxidation of isobutylene or tertiary butyl alcohol is ordinarily carried out at super-atmospheric pressures, e.g. the effluent gas leaves the reactor at pressures up to 50 psig, generally less, e.g. 15 psig or below, and, as mentioned, at elevated temperatures of the order of 300° to 500° C. The gaseous stream issuing from the catalytic reactor at the reaction pressure and temperature is suitably cooled somewhat before introducing it into the first quenching stage, but this cooling is not sufficient to cause any condensation of water. Typically, the gaseous stream is cooled to 160° to 120° C. and it is then introduced into the aqueous liquid contained in the first quenching zone which is substantially at the catalytic reactor exit pressure. The aqueous liquid used in the first quenching zone is maintained at a temperature sufficiently low to cause condensation of a substantial portion of the water vapor in the gaseous mixture introduced into it, e.g. a temperature of the order of 35° to 60° C., which temperature is suitably maintained by conventional means, e.g. by a cooler in the circuit through which the aqueous liquid circulates from the bottom of the quenching zone to its upper portion in order continuously to maintain a liquid body in the zone for contact with the gaseous stream. The net production of water is withdrawn from the quenching zone as are the uncondensed vapors which are passed to compressing means in which their pressure is increased, e.g. to a pressure 50 to 70 psi higher than the pressure in the first quenching zone. The thus pressured vapors are then fed to a second quenching zone which, like the first quenching zone, is provided with circulating means for maintaining a continuous body of liquid in that zone for contact with the vapor stream coming from the compressing means at the second-stage pressure. The liquid in the subsequent quenching zone can be at the same temperature as the liquid in the first zone but, preferably, the temperature decreases from zone to zone. Thus, the circulating liquid is cooled, e.g. in the manner described above and is preferably maintained at a temperature of 45° to 55° C., i.e. 5° to 10° C. cooler than the first quenching zone. Additional water vapor is condensed in the second quenching zone and withdrawn from it. The uncondensed vapor is further compressed to increase its pressure and it is then introduced into the liquid body in the third quenching zone. The liquid body in the third quenching zone is maintained, e.g. by circulation through a conventional cooler in the manner of the first and second zones, at a temperature of 35° to 45° C. and the prevailing pressure in the third zone is 125 to 145 psig, i.e. 60 to 80 psi greater than the pressure in the second quenching zone.

While three quenching zones are ordinarily sufficient to eliminate substantially all of the water vapor from the methacrolein-containing gaseous stream originally issuing from the catalytic reactor, additional quenching zones or stages may be provided, if desired, with the pressure of the vapors being gradually increased in passing from zone to zone, and the temperatures of the liquid used in the quenching zones being preferably gradually decreased, to an eventual minimum temperature of approximately 35° C. and an eventual maximum pressure of the order of 250 psig.

The pressurizing of the vapors or gases being treated to increase their pressure between the several quenching stages can be effected by any conventional means, as will be known to persons skilled in the art, but it is advantageously carried out by means of a single multistage contrifugal compressor or turbo blower of known construction, such as described, for example in "Compressed Air and Gas Handbook" published by the Compressed Air and Gas Institute, New York, N.Y., Third Edition, 1961 (revised 1966), pp. 3-1 et seq.

The recovered water from the several quenching stages is suitably collected and may be treated in conventional manner for recovery of any dissolved organic materials such as minor amounts of methacrolein, acetic acid and methacrylic acid.

The methacrolein-containing vapor stream issuing from the last quenching zone, which contains substantially all of the methacrolein present in the gaseous stream originally fed to the quenching system, as well as other noncondensed materials, such as unreacted isobutylene, unreacted oxygen, nitrogen and other non-condensible inert gases, is subjected to scrubbing with a liquid absorbent in conventional manner, for example with a ketone as described in Roelen et al, U.S. Pat. No. 3,162,514, or with a hydrocarbon as described in Roelen et al. U.S. Pat. No. 3,218,357, or with an alcohol, acetone or acetonitrile as described in Sato et al. U.S. Pat. No. 3,828,099. Preferably, however, the vapor stream from the last quenching zone is scrubbed with acetic acid in accordance with the process described in my co-pending application entitled "Recovery of Methacrolein" being filed on even date herewith and identified as U.S. Pat. No. 4,092,132, the disclosure of which application is incorporated herein by reference. One of the advantages of the process of this invention which, as described, involves increasing the pressure of the gaseous effluent issuing from the catalytic reactor in which methacrolein is produced is that it provides a methacrolein-containing, substantially anhydrous gas mixture, which is at a pressure which facilitates its recovery by scrubbing with an organic solvent such as those mentioned in the preceding portion of this paragraph, and especially in the case of scrubbing with acetic acid by the process disclosed in the above-mentioned co-pending application. While the content of water in the gaseous mixture produced in accordance with the process of this invention is in no way critical, it is possible readily to produce a gas mixture of this character containing only one volume % or less water, notwithstanding the absence of any cooling with refrigerants, i.e. cooling to temperatures below the temperature of readily available sources of water.

The invention will be more fully understood by reference to the accompanying drawing which illustrates, diagrammatically, an illustrative embodiment of a multi-stage quenching system suitable for carrying out the process of the invention, the drawing also showing a typical relationship of the quenching system to the reactor in which the methacrolein-containing effluent to be quenched is produced.

Referring to the drawing, the reference numeral 20 designates the vapor outlet line from a catalytic reactor (not shown) of any convenient type containing a catalyst suitable for the conversion of isobutylene or tertiary butyl alcohol to methacrolein. It will, of course, be understood that the oxidation of isobutylene or tertiary butyl alcohol and the catalyst employed for such oxidation form no part of the present invention, which is applicable to the treatment of water vapor-containing effluents from any vapor-phase catalytic reaction which produces methacrolein from isobutylene or tertiary butyl alcohol. Reference has been made above to Ishii et al. U.S. Pat. No. 3,972,920 merely because this patent is exemplary of recent developments in this technology. The process of this invention is equally applicable to effluents from catalytic oxidations involving the use of other catalysts, e.g. the catalyst described in Callahan et al at U.S. Pat. No. 2,941,007 and the numerous other catalysts which have been proposed and are well known to persons skilled in the art. In the embodiment illustrated in the drawing, the reaction effluent issuing from the reactor via line 20 passes into indirect heat exchange in heat exchanger 24 in which the effluent is cooled. Typically a reaction effluent at a temperature of the order of 400° C. is cooled by such heat exchange to a temperature of the order of 120° to 160° C. From the cooler 24 the effluent passes via line 26 into the lower portion of the first quenching tower 28 through which is circulated a stream of aqueous liquid, e.g., condensate from prior quenching operations, the effluent from line 26 being introduced into the lower portion of the tower 28. The term "tower" is used herein to designate any liquid-vapor contact apparatus, of conventional type, such as a scrubber, provided with means for increasing the gas-liquid contact such as bubble cap trays, trickle trays, shed trays, sieve trays, valve trays, and the like, or packing such as Berl saddles, Raschig rings, and the like. Preferably the tower contains at least 4 actual plates or contact stages. To provide the circulating stream, there is connected with the lower and upper portion of tank 28 a liquid circuit comprising outlet line 32 and recycle line 34 containing a pump (not shown) and in which is interposed a cooler 36 which provides a means for controlling the temperature of the circulating stream, typically within the range of 40° to 60° C. Upon contact with the aqueous liquid in tower 28, some of the water vapor contained in the effluent entering via line 20 is cooled and condensed and the net production of liquid is withdrawn through line 38. At the same time, the non-condensed portion of the effluent leaves tower 28 through outlet line 40 substantially at the pressure existing in reactor 10 and passes to a compressing means for increasing its pressure, typically by 55 to 75 psi. In the embodiment illustrated, the compressing means takes the form of a multi-stage centrifugal compressor or turbo blower 42 and the line 40 is connected to compressor 42 to supply the non-condensed gases to the inlet of its first stage. From the outlet of the first stage of the compressor the uncondensed gases exit through line 44 and pass into the lower portion of quench tower 46 which, like quench tower 28, contains a circulating aqueous stream and is provided with a liquid circuit comprising an outlet line 50 and a recycle line 52 containing a pump (not shown) and a cooler 54 which maintains the temperature of the circulating stream typically at, for example, 45° to 55° C. The net production of liquid in quench tower 46 is withdrawn via line 56 which connects with line 38 from quench tower 28. The still uncondensed portions of the effluent leave quench tower 46 through line 60 and pass to the inlet of a further stage of the compressor 42 and are typically increased in pressure by 70 to 90 psi and leave the outlet of the further stage of the compressor through line 65 and are led into contact with the aqueous stream contained in the third quench tower 72, this tower being connected with an outlet line 74 and a recycle line 76 containing a pump (not shown) and a cooler 78 which functions to maintain the circulating stream typically at a temperature of the order of 35° to 45° C. The net formation of liquid in the circulating stream resulting from the condensation of most of the water vapor remaining in the gaseous stream fed to tower 72 is withdrawn through line 80 which communicates with line 38 carrying the liquid produced in quench towers 28 and 46. Typically more than 95% of the water has been condensed at this point. At the same time, the substantially dehydrated gaseous components of the effluent originally fed through line 26 and containing substantially all, typically at least about 98%, of the methacrolein originally contained in the effluent, leave the quenching system through line 85. Typically this gaseous mixture is treated to recover its methacrolein content and, since the mixture contains unreacted isobutylene, this isobutylene is typically recycled to the oxidation reactor 10 (by means not shown) after the methacrolein has been separated from it. As previously mentioned, the methacrolein may be recovered by any convenient means such as by scrubbing with various organic solvents as described in Roelen et al U.S. Pat. Nos. 3,162,514 and 3,218,357 or Sato et al. U.S. Pat. No. 3,828,099. The above mentioned co-pending application, however, provides a particularly efficient and effective scrubbing system involving the use of acetic acid as a scrubbing liquid and the gaseous mixture leaving quench tower 72 is at a temperature and a pressure particularly advantageous for the acetic acid scrubbing process so that it can be directly fed to the acetic acid scrubber, e.g. of the type described in the co-pending application.

The accumulated condensed aqueous liquid in line 38 can be discarded and incinerated to remove its organic content, or it can be treated, if desired, to recover the contained organic compounds in conventional manner.

The feed to the quenching process of the invention will, as previously mentioned, consist of the effluent mixture from the catalytic reactor in which the methacrolein has been produced by the catalytic oxidation of isobutylene or tertiary butyl alcohol and it will, of course, vary in the relative proportions of the several components depending upon the reaction conditions, the specific catalyst employed, the relative composition of the feed to the oxidation, and the like. The process of the invention, however, is applicable to any such effluent regardless of the relative proportions of its components since it will always contain water vapor, particularly when steam is one of the components of the feed to the oxidation. Actually the process of the invention is of particular application to the effluent from an oxidation with a steam-containing feed since the quantity of water vapor in the effluent is obviously relatively high since it contains the steam in the feed plus water vapor generated in the oxidation reaction itself. By way of illustration, however, a typical effluent to which the process of this invention is most advantageously applied contains 1.5 to 6 volume % methacrolein, 10 to 40 volume % water, 0.2 to 3 volume % unconverted isobutylene, 4 to 8 volume % oxygen, and the remainder inert gases, e.g., nitrogen, CO, $CO_2$ plus very small amounts, 1% or less, of vapors of miscellaneous organic by-products, including acetic acid. The process of this invention makes it possible to separate up to 98% of the water vapor and to leave up to 99% of the methacrolein in non-condensed form for later recovery from the dehydrated gaseous stream. Typically and preferably, the amount of water in the liquid effluent, e.g. in line 23, produced in the process of the invention is at least 85 weight %, and the amount of methacrolein is at most 5%, respectively of the water and methacrolein contained in the feed.

The following specific example of practical application of the process will serve to give an even fuller understanding of the invention, but it is to be understood that it is given by way of illustration only and is not to be construed in any way as limitative of the invention. In the example all parts are by weight, unless otherwise indicated.

EXAMPLE

In a system such as illustrated in the drawing, a gaseous reaction effluent comprising approximately 10% water vapor and 5.4% methacrolein, and the balance being oxygen, inert gases, unreacted isobutylene and organic by-products including methacrylic acid and acetic acid, resulting from the catalytic oxidation of isobutylene with air in the presence of steam, continuously flows at the rate of about 1,000 parts per hour via line 20 at a temperature of 380° C. and under a pressure of 12.3 psig into indirect heat exchange in heat exchanger 4 and its temperature is reduced to 140° C. From the cooler 24 the effluent gases pass via line 26 into the lower portion of the first quenching tower 28 containing 6 actual plates in the form of sieve trays and in which there is a downwradly-flowing circulation stream of water at a temperature of about 53° C. maintained by continuous pump-around flow of the aqueous stream at a rate of about 6,400 parts per hour through cooler 36. In this first quenching zone 52.2 parts per hour of the water vapor contained in the effluent is condensed and absorbed in the aqueous stream, about 0.2 parts per hour of the methacrolein and organic by-products also being dissolved in the liquid stream. The remainder of the gaseous effluent at a pressure of about 10 psig then passes to the initial section of a multi-stage compressor 42 where its pressure is increased to 67 psig and it then flows from the outlet of this section of the compressor to the lower portion of the second quenching tower 46 of the same construction as tower 28 containing a downwardly-flowing stream of aqueous quench liquid maintained at a temperature of about 50° C. by continuous pump-around flow through cooler 54 at about 5,100 parts per hour. In the second quenching zone about 34.4 parts per hour of water vapor are condensed and absorbed and about 0.5 parts per hour of methacrolein and organic by-products are also dissolved in the aqueous quenching liquid. The remainder of the gaseous effluent at a pressure of about 65 psig then flows to the inlet of the second section of compressor 42 and, upon exiting from the compressor outlet at a pressure of 134 psig, passes to the lower portion of the third quenching tower 72, also of the same construction as tower 28, which contains a downwardly-flowing stream of aqueous quenching liquid maintained at a temperature of about 40° C. by pump-around flow through cooler 78 at the rate of about 5,700 parts per hour. In quenching tower 72 a final 8.3 parts per hour of water vapor are condensed and absorbed in the aqueous quenching liquid, along with about 0.4 parts of methacrolein and organic by-products. The net aqueous "make" from the three quenching towers is combined and withdrawn via line 38 at the rate of 96.5 parts per hour, the withdrawn stream being composed of 94.9 parts water, 1.1 parts methacrolein and 0.5 parts organic by-products, representing a removal of more than 96% of the water vapor contained in the effluent orignally fed to the system and only 2% of the methacrolein. Essentially all of the organic by-products are also removed.

At the same time, the gaseous effluent from the third quenching tower is at a temperature of about 40° C. under a pressure of 132 psig and is withdrawn at the rate of 903.5 parts per hour. It contains only 0.4% water vapor and essentially all of the methacrolein fed to the system.

In the foregoing example there are used quenching towers containing 6 actual plates or contact stages and, as previously mentioned, ordinarily each tower zone should contain at least 4 actual plates or contact stages. Preferably each contains 5 to 8 actual plates or contact stages. A greater number of plates may be provided, the total number being limited only by practical and economic considerations, as will be apparent to persons skilled in the art. In the example the flow of gas or vapor and aqueous quenching liquid is such that the temperature rise of the quenching liquid across each quenching tower is 10° C. Ordinarily, it should be at least about 5°, preferably 8° to 25° C.

It will, of course, be understood that various changes and modifications may be made with respect to what has been described above and illustrated in the drawing without departing from the invention as defined in the appended claims. For example, while the process described involves a sequence of operations carried out under conditions which minimize the possibility of polymerization, a polymerization inhibitor, such as hydroquinone or other inhibitor well known to persons skilled in the art, may be added to any of the streams as desired. It is intended, therefore, that all matter contained in the foregoing description and in the drawing shall be interpreted as illustrative only and not in a limiting sense.

What is claimed is:

1. A process for the removal of water vapor from a gaseous stream under superatmospheric pressure up to about 50 psig and at a temperature of about 300°–500° C. produced by the catalytic oxidation of isobutylene or tertiary butyl alcohol and containing methacrolein, which comprises introducing said gaseous stream sequentially into a plurality of quenching zones arranged in series and each containing an aqueous stream with which said gaseous stream comes into direct contact in a plurality of contact stages, while increasing the superatmospheric pressure of said gaseous mixture between each of said plurality of quenching zones to a maximum pressure of about 250 psig while cooling said gaseous stream to a minimum temperature of about 35° C., the aqueous stream in each of said quenching zones being comprised of water containing dissolved components of said gaseous stream, whereby said gaseous mixture is introduced sequentially into said zones at a graduated increased pressure and the superatmospheric pressure in each succeeding zone is greater than the superatmospheric pressure in the preceding zone.

2. A process as defined in claim 1, wherein the water in said zones is maintained at gradually decreasing temperature.

* * * * *